US006874505B1

(12) United States Patent
Fenwick et al.

(10) Patent No.: US 6,874,505 B1
(45) Date of Patent: Apr. 5, 2005

(54) SURGICAL DRAPE SYSTEM WITH POUCH

(75) Inventors: Christopher Dale Fenwick, Alpharetta, GA (US); Casey Lynn Dusenbery, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/664,562

(22) Filed: Sep. 19, 2003

(51) Int. Cl.[7] ............................................... A41D 13/12
(52) U.S. Cl. ...................... 128/849; 128/850; 128/853
(58) Field of Search ................................ 128/849, 850, 128/851, 852, 853, 854, 855, 856; 2/48

(56) References Cited

U.S. PATENT DOCUMENTS

| | | | |
|---|---|---|---|
| 2,585,946 A | * | 2/1952 | Liberman .................... 434/95 |
| 3,503,391 A | * | 3/1970 | Melges ....................... 128/852 |
| 3,561,439 A | | 2/1971 | Bayer |
| 3,565,067 A | | 2/1971 | Bayer |
| 3,791,382 A | | 2/1974 | Collins |
| 3,889,667 A | | 6/1975 | Collins |
| 4,051,845 A | | 10/1977 | Collins |
| 4,570,628 A | * | 2/1986 | Neal .......................... 128/853 |
| 4,596,245 A | * | 6/1986 | Morris ....................... 128/852 |
| 4,664,103 A | | 5/1987 | Martin et al. |
| 4,869,271 A | | 9/1989 | Idris |
| 4,905,710 A | | 3/1990 | Jones |
| 4,944,311 A | | 7/1990 | Eldridge, Jr. et al. |
| 4,957,120 A | * | 9/1990 | Grier-Idris ................. 128/849 |
| 5,002,069 A | | 3/1991 | Thompson et al. |
| 5,010,899 A | | 4/1991 | Thompson |
| 5,074,316 A | | 12/1991 | Dowdy |
| 5,170,804 A | * | 12/1992 | Glassman ................... 128/849 |
| 5,339,831 A | | 8/1994 | Thompson |
| 5,345,946 A | | 9/1994 | Butterworth et al. |
| 5,377,694 A | | 1/1995 | Bark |
| 5,494,050 A | | 2/1996 | Reyes |
| 5,530,968 A | * | 7/1996 | Crockett ......................... 2/46 |
| 5,618,278 A | * | 4/1997 | Rothrum ..................... 604/356 |
| 5,816,253 A | | 10/1998 | Sosebee |
| 5,871,014 A | | 2/1999 | Clay et al. |
| 5,916,202 A | | 6/1999 | Haswell |
| D416,375 S | * | 11/1999 | McMaster ................... D2/864 |
| 5,985,395 A | | 11/1999 | Comstock et al. |

(Continued)

FOREIGN PATENT DOCUMENTS

EP 0186582 A2 7/1986

(Continued)

*Primary Examiner*—Henry Bennett
*Assistant Examiner*—Camtu Nguyen
(74) *Attorney, Agent, or Firm*—Scott B. Garrison

(57) ABSTRACT

A surgical drape system is provided including a drape component and a pouch component. The drape component has a main sheet portion and may have a fenestration for providing access to an operative site on a patient. The pouch component may be created from a rear panel and a front panel superimposed and partially sealed one to the other to provide a pouch having an open top and partially open sides. The rear panel is attached to the drape in proximity to the fenestration and holds the pouch in place on the drape. A number of spaced apart fasteners are disposed upon at least one of the panels proximate to the open top. The fasteners are for fastening sections of the front and rear panel to one another thus establishing alternating fastened and unfastened regions in the open top.

24 Claims, 4 Drawing Sheets

U.S. PATENT DOCUMENTS

| | | |
|---|---|---|
| 5,988,172 A | 11/1999 | Sosebee |
| 6,129,085 A | 10/2000 | Jascomb |
| 6,179,819 B1 | 1/2001 | Haswell |
| D437,410 S | 2/2001 | Watson et al. |
| 6,199,553 B1 | 3/2001 | Hafer et al. |
| 6,308,875 B1 | 10/2001 | Almo |
| 6,314,958 B1 | 11/2001 | Harroll et al. |
| D473,364 S * | 4/2003 | Conte .......................... D2/864 |

FOREIGN PATENT DOCUMENTS

| | | |
|---|---|---|
| EP | 0281331 A1 | 9/1988 |
| EP | 0765140 B1 | 2/1998 |
| EP | 0621011 B1 | 6/1999 |
| EP | 0910303 B1 | 3/2002 |
| EP | 0923351 B1 | 3/2003 |
| WO | WO 90/06731 | 6/1990 |
| WO | WO 96/01595 | 1/1996 |
| WO | WO 96/38096 | 12/1996 |
| WO | WO 97/09001 | 3/1997 |
| WO | WO 97/42904 | 11/1997 |
| WO | WO 98/08457 | 3/1998 |
| WO | WO 98/41162 | 9/1998 |
| WO | WO 99/37234 | 7/1999 |
| WO | WO 02/41800 | 5/2002 |

* cited by examiner

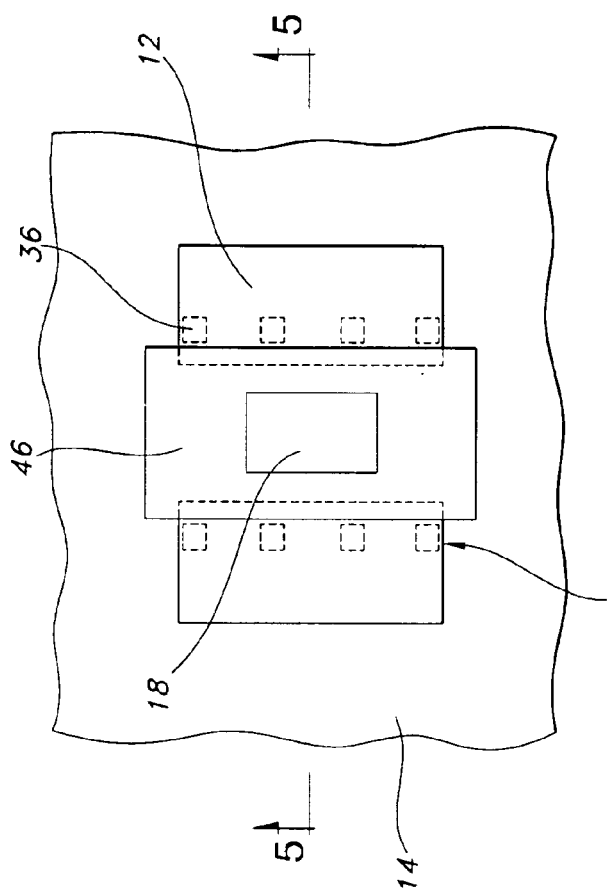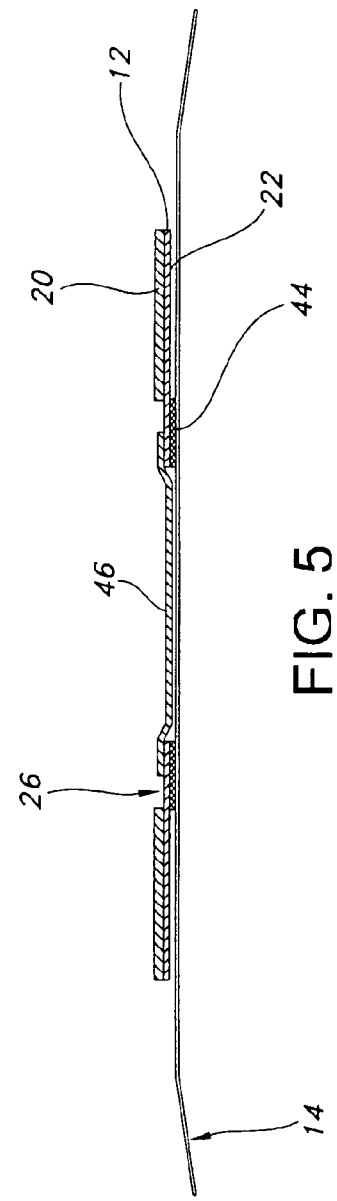

SURGICAL DRAPE SYSTEM WITH POUCH

BACKGROUND OF THE INVENTION

The present invention relates generally to surgical drapes, and more particularly to surgical drape systems adapted to work in conjunction with fluid collection pouches.

Drapes are used during surgical procedures to create and maintain a sterile environment about the surgical site. Draping materials are selected to create and maintain an effective barrier that minimizes the passage of microorganisms between non-sterile and sterile areas. To be effective, a barrier material should be resistant to blood, aqueous fluid, and abrasion, as lint-free as possible, and drapeable. When used during surgery, drapes prevent blood and other bodily fluids from contaminating the sterile field.

A variety of surgical drapes exist, but most share several common features. Most drapes are made of a water-repellent or water-impermeable material, or are coated with such a material, to prevent the passage of bodily fluids as well as contaminating microorganisms. Many of today's surgical drapes are made of disposable nonwoven fabrics, plastic film, or papers.

Surgical drapes will commonly have an opening or aperture (more commonly known in the medical field as a "fenestration") through which the surgical procedure is performed. The surgical procedures performed often result in blood and other fluids being produced in the surgical site either directly from the patient or from irrigation fluids used to flush the site. A simple way to control these fluids is to provide towels, or other absorptive materials, in and around the surgical site. When the surgical procedure is expected to involve more fluid run-off than can be absorbed in this way, one or more pouches can be attached to the drape and/or be an integral part of the drape as it is made.

During the procedure electric cords, tubes, and suction lines running along the patient are usually clamped or tied to the edges of the outer sheet on the surgical table. These cords or lines can become entangled, and when pulled may cause devices to fall to the floor and become non-sterile. The clamps and ties are usually not versatile or strong enough to allow easy addition or removal of tubes and electrical lines. This results in delay in surgery while operating room personnel undo and re-affix clamps. Providing drapes that are suitable for use in surgical procedures having adequate mechanisms to secure such cords and lines remains a concern of health care professionals.

SUMMARY OF THE INVENTION

The present invention is drawn to a surgical drape system having a drape component and a pouch component. The drape component has a main sheet portion for covering at least a substantial portion of a patient. The drape component may have a fenestration for providing access to an operative site on a patient. The pouch component may be created from a rear panel and a front panel superimposed one over the other. The two panels would be sealed to one another along a bottom edge and partially up opposing side edges. This configuration provides a pouch having an open top and partially open sides. The rear panel is attached to the drape in proximity to the fenestration and holds the pouch in place on the drape. A number of spaced apart fasteners are disposed upon at least one of the panels proximate to the open top. The fasteners are for fastening sections of the front and rear panel to one another thus establishing alternating fastened and unfastened regions in the open top. In some embodiments at least a portion of at least one of the panels may be clear.

In another embodiment, the present invention is drawn to a surgical drape system having a drape component and a tubing caddy. The drape component has a main sheet portion for covering at least a substantial portion of a patient. The drape component may have a fenestration for providing access to an operative site on a patient. The tubing caddy is attached to the drape in proximity to the fenestration. The caddy is provided with a plurality of spaced apart fasteners disposed thereon for interweaving and holding medical lines and tubes. The caddy may be fashioned from overlapping panels sealed to one another along a bottom edge and partially up opposing side edges.

In still another embodiment, the present invention is drawn to a surgical drape system having a drape component and a pouch component. The drape component has a main sheet portion for covering at least a substantial portion of a patient. The drape component may have a fenestration for providing access to an operative site on a patient. The pouch has a top, a bottom, and sides and is attached to the drape in proximity to the fenestration. The bottom and at least a portion of the sides of the pouch are sealed to permit liquid to be held within the pouch. The top and at least another portion of the sides have fasteners disposed thereon for holding medical lines and tubes.

Such a surgical drape system may be found useful in surgical procedures where it is desirable to perform any or all of; collection of excess fluids that may escape from a surgical site, provide a means to secure surgical tubes and lines in specific positions throughout the surgical procedure, as well as provide a means to store surgical instruments and/or materials to be used in the surgical procedure.

These and other objects are achieved by the surgical drape system disclosed and claimed herein.

BRIEF DESCRIPTION OF THE DRAWINGS

FIG. 4 is a plan view depicting the attachment of an exemplary pouch to an exemplary drape of the FIG. 1 surgical drape system.

FIG. 5 is a section view taken through line 5—5 of FIG. 4.

DETAILED DESCRIPTION OF THE INVENTION

Figure 1:
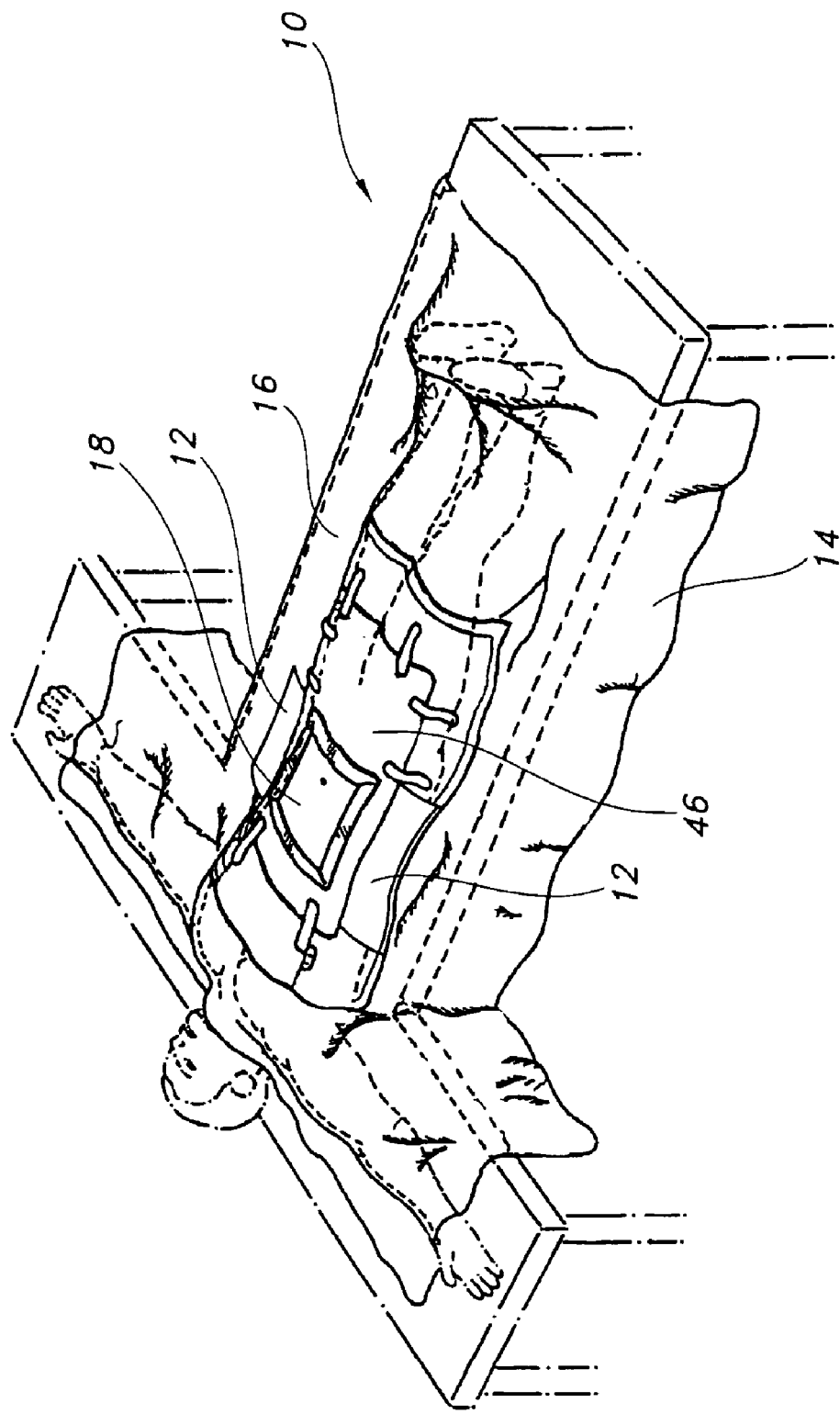
FIG. 1 is a diagrammatic view of an exemplary surgical drape system in use on a patient in accordance with the present invention.

Referring to FIG. 1, the present invention is directed to an improved surgical drape system 10 that includes a pouch 12 adapted to be used with a drape 14. The pouch 12 is affixed to a drape 14 selected so as to be appropriate to the type of surgery performed. The pouch 12 may be made to serve a number of purposes. A pouch in accordance with the present invention may be used to collect excess fluids that may escape from a surgical site thus minimizing contamination of the operating room by preventing the fluids from dripping onto the floor. Collection of patient bodily fluids, including blood, would also be beneficial to operating personnel in that it may help minimize the potential transfer of blood-borne pathogens. The pouch may also serve as a means to secure surgical tubes and lines in various configurations so that they remain in position throughout the surgical procedure. Another use for the pouch described herein is for storage of surgical instruments and/or materials to be used in the surgical procedure. Such a pouch may be useful for any one individual or any combination of these purposes.

As such, it can be seen on FIG. 1 that the drape system 10 includes a drape 14 having a main sheet portion 16 for covering at least a substantial portion of a patient undergoing a surgery. The drape configuration may vary based upon the type of surgical procedure to be performed and/or the preference of the surgical team. In most instances, however, especially those wherein the pouch 12 is used to collect bodily fluids, the drape 14 would be provided with a fenestration 18. The fenestration 18 provides access to the appropriate operative site on the patient.

Figure 2:
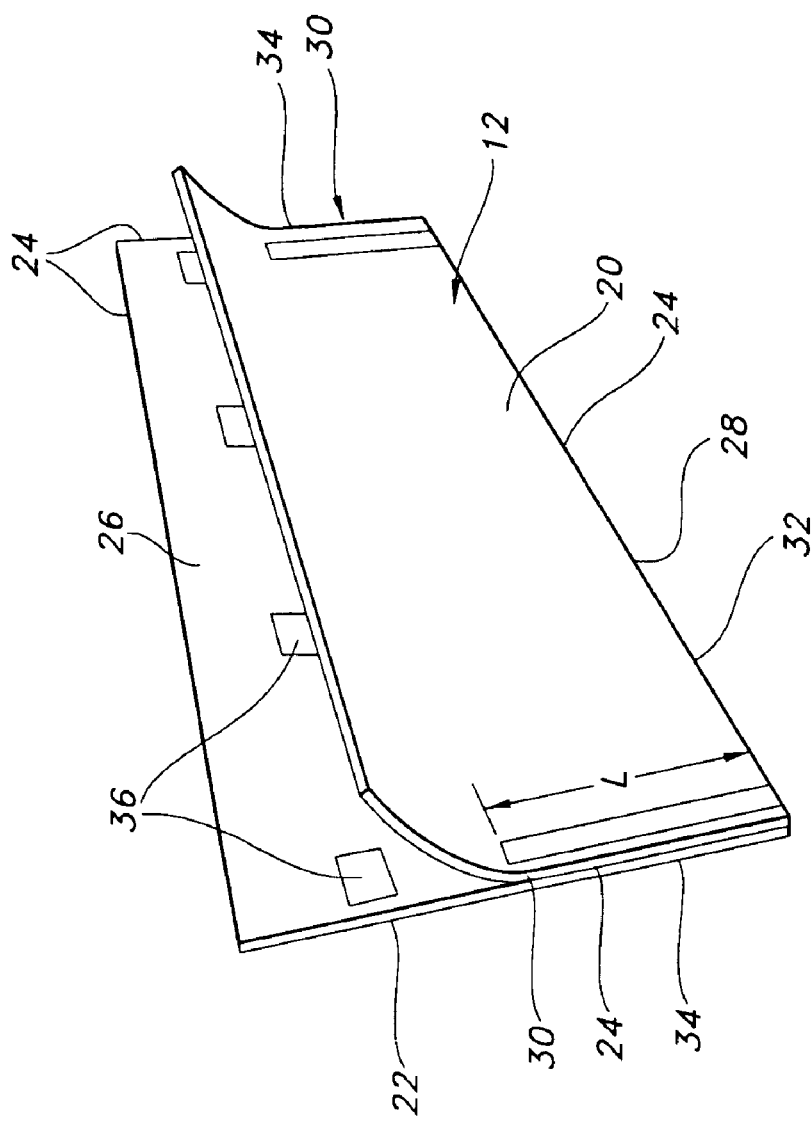
FIG. 2 is a diagrammatic view of an exemplary pouch for use on the surgical drape system of FIG. 1.

Looking now to FIG. 2, it can be seen that the pouch 12 may be constructed in a variety of ways, including as a bag or a series of panels attached to one another, such as front panel 20 and rear panel 22. In this embodiment, panels 20 and 22, each having a periphery 24 are superimposed one over the other and sealed to one another along at least a portion of their peripheries 24. The superimposed and sealed panels together form the pouch 12.

Panels 20 and/or 22 may be constructed so as to be opaque, translucent, or transparent in whole or in part. The materials for constructing the pouch are well known and understood by those skilled in the art. Some suitable materials for manufacturing the pouch include but are not limited to films and nonwoven materials. In embodiments adapted to hold instruments for use in the intended procedure, it may be desirable for the front panel 20 to be transparent to better assist in the visual identification of the instruments contained within the pouch 12. As such a transparent film would be useful for this purpose.

Still looking to FIG. 2, pouch 12 is seen to have a top 26, a bottom 28, and sides 30. Though the FIGS. depict the pouch 12 as rectangular in shape and having four sides, there is no need for this configuration. The pouch may be of any shape desirable for the surgical procedure and may have more or less than two sides, a top, and a bottom. In embodiments adapted to collect and retain fluid, the bottom 28 is sealed along edge 32 and the sides 30 are sealed for some length "L" along side edges 34. The length "L" is dependent upon the pouch design. Pouches designed to collect and retain significant amounts of fluid would be sealed a greater length "L" than those designed to collect and retain a lesser quantity of fluid. For example, in some embodiments the seal length "L" may extend for as much as about half way up the side edges 34, in other embodiments the seal length may extend for as much as about seventy-five percent up the side edges. As stated, the seal length "L" may be any length deemed appropriate by those skilled in the art. Moreover, some embodiments of the pouch 14 may be configured to incorporate a drain and an appropriate fitting (not shown) to drain fluids collected. It should be understood that the existence of a drain would have a bearing upon the need for a specific seal length "L". As such, a shorter seal length "L" could be used even though larger quantities of fluids might be anticipated in the procedure because the drain would function to minimize the amount of fluid retained within the pouch.

Figure 3:
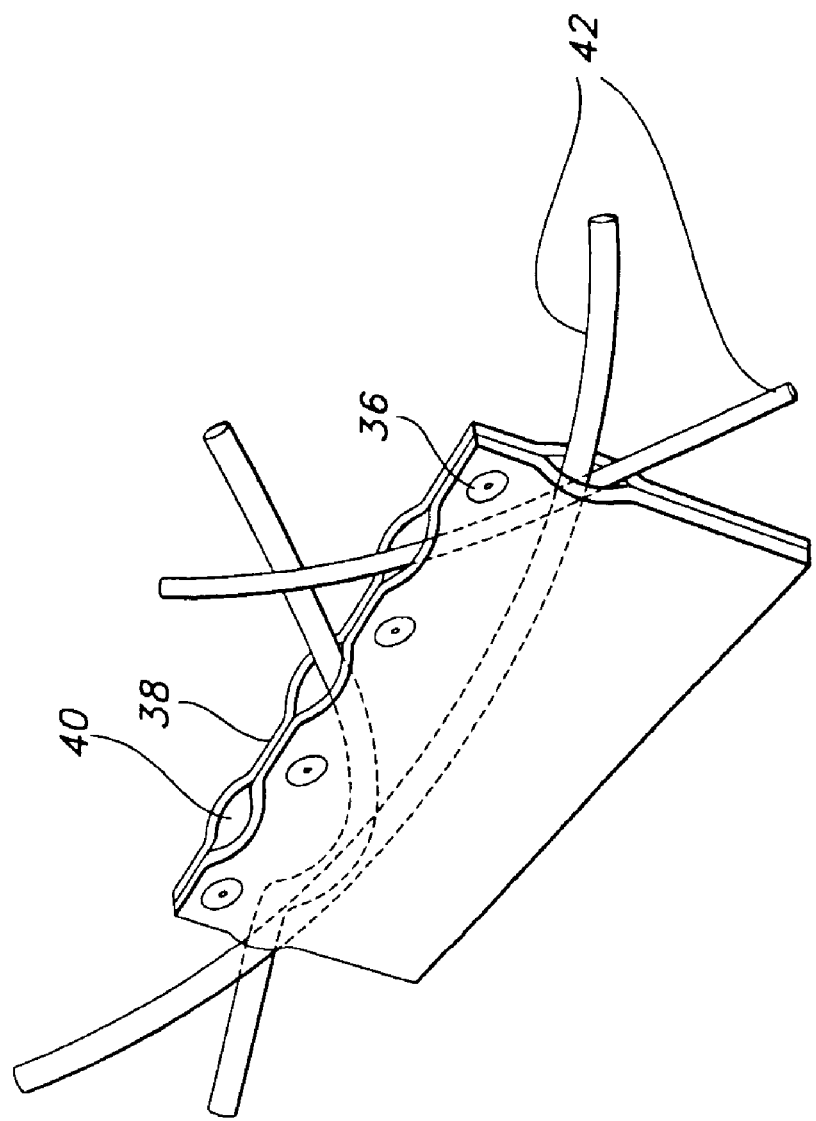
FIG. 3 is a diagrammatic view of an exemplary pouch for use on the surgical drape system of FIG. 1 depicting surgical tubes and lines being held in one possible configuration.

Still looking to FIG. 2, it can be seen that the top 26 and at least a portion of the sides 30 are open. Disposed upon at least one of the panels 20 or 22 are a plurality of spaced-apart fasteners 36. The fasteners 36 are situated so as to fasten sections of the front panel 20 and the rear panel 22 together. This arrangement creates a series of alternating fastened regions 38 and unfastened regions 40, as depicted in FIG. 3, in the otherwise open top 26. The number of fasteners 36 and the distance between each is dependent upon the drape design and/or the pouch design itself. The alternating fastened and unfastened regions enable the surgical team to selectively choose whether or not to fasten any combination of fasteners 36 independent of one another, thus effectively forming a tubing caddy, enabling the tubes and lines 42 to be arranged in any number of desirable configurations. An example of such a configuration can be seen in FIG. 3.

The fasteners 36 may be selected from any number of suitable alternatives. For example, FIG. 2 depicts hook and loop type fasteners, whereas FIG. 3 depicts snap type fasteners. The fasteners themselves may be designed to be capable of repeated fastening and unfastening events without failure. Examples of this design may include but are not limited to snaps, hook and loop, and clips. Alternatively, the fasteners may be designed for limited fastening and unfastening events. Examples of these include adhesives as well as adhesive tape (not shown). In some cases, these adhesives may be designed for a single fastening only.

The pouch 12 may be a stand-alone component that is attached to the drape 14 just prior to the surgical procedure when the patient is being prepped. This would enable optimal placement of the pouch and repositioning of the pouch if desired by the surgical team. As such, the pouch 12 may be attached to the drape 14 by an adhesive 44, adhesive tape, or other suitable alternative. The pouch may also be fastened to the drape during manufacture. Looking now to FIGS. 4 and 5, one possible construction is depicted. In this embodiment, the adhesive 44 is affixed to an outside surface of panel 22 proximate to the top 26. The adhesive 44 is contacted to the drape 14 and subsequently adheres the pouch 12 to the drape. To ensure proper fluid runoff, fenestration reinforcement material 46 (if provided) may be caused to overlap the interface of the drape and pouch as shown in FIGS. 4 and 5. One alternative may be to adhere the pouch 12 directly to the fenestration reinforcement material 46. This is easily accomplished by affixing the adhesive 44 to the surface of panel 22 that contacts the fenestration reinforcement material 46.

It is contemplated that the surgical drape system constructed in accordance with the present invention will be tailored and adjusted by those of ordinary skill in the art to accommodate various levels of performance demand imparted during actual use. Accordingly, while this invention has been described by reference to certain specific embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

We claim:

1. A surgical drape system comprising:
    a drape having a main sheet portion for covering at least a substantial portion of a patient, the drape having a fenestration for providing access to an operative site;
    a rear panel and a front panel superimposed one over the other and sealed to one another along a bottom edge and partially up opposing side edges so as to form a pouch having an open top and partially open sides, the rear panel attached to the drape in proximity to the fenestration;

a plurality of spaced apart fasteners disposed upon at least one of the panels proximate to the open top for fastening sections of the front and rear panel to one another thus establishing alternating fastened and unfastened regions in the open top.

2. The system of claim 1 wherein at least a portion of at least one of the panels is clear.

3. The system of claim 1 wherein the fasteners comprise hook and loop type fasteners.

4. The system of claim 1 wherein the fasteners comprise snap type fasteners.

5. The system of claim 1 wherein the fasteners comprise lengths of adhesive material.

6. The system of claim 5 wherein the adhesive material comprises adhesive tape.

7. The system of claim 1 wherein the pouch is capable of retaining liquids.

8. The system of claim 1 wherein the rear panel comprises an adhesive for attaching the pouch to the drape.

9. The system of claim 8 wherein the adhesive comprises adhesive tape.

10. The system of claim 1 wherein the pouch is adjustably attached to the drape.

11. A surgical drape system comprising:
a drape having a main sheet portion for covering at least a substantial portion of a patient, the drape having a fenestration for providing access to an operative site;
a tubing caddy attached to the drape in proximity to the fenestration having a plurality of spaced apart fasteners disposed thereon for interweaving and holding medical lines and tubes, the caddy further comprising overlapping panels sealed to one another along a bottom edge and partially up opposing side edges.

12. The system of claim 11 wherein at least a portion of at least one of the panels is clear.

13. The system of claim 11 wherein the fasteners comprise hook and loop type fasteners.

14. The system of claim 11 wherein the fasteners comprise snap type fasteners.

15. The system of claim 11 wherein the fasteners comprise length of adhesive material.

16. The system of claim 15 wherein the adhesive material comprises adhesive tape.

17. The system of claim 11 wherein the caddy is capable of retaining liquids.

18. The system of claim 11 wherein the caddy comprises an adhesive for attaching to the drape.

19. The system of claim 18 wherein the adhesive comprises adhesive tape.

20. The system of claim 11 wherein the caddy is adjustably attached to the drape.

21. A surgical drape system comprising:
a drape having a main sheet portion for covering at least a substantial portion of a patient, the drape having a fenestration for providing access to an operative site;
a pouch having a top, a bottom, and sides, attached to the drape in proximity to the fenestration, the bottom and a portion of the sides being sealed to permit liquid to be held within the pouch, the top and a second portion of the sides having a fastener disposed thereon for holding medical lines and tubes.

22. The system of claim 21 wherein the fastener comprises a hook and loop type fastener.

23. The system of claim 21 wherein the fastener comprises an adhesive material.

24. The system of claim 23 wherein the adhesive material comprises adhesive tape.

* * * * *